United States Patent [19]
Ota et al.

[11] Patent Number: 5,846,359
[45] Date of Patent: Dec. 8, 1998

[54] ULTRASONIC DIRECT FIXING OF REAGENT LAYER AND METHOD FOR PREPARING PEEL TYPE TEST PIECE

[75] Inventors: Minoru Ota; Yoshinori Takahashi, both of Kyoto; Yoshihiko Higuchi, Osaka; Takashi Tsujii, Kyoto, all of Japan

[73] Assignee: Kyoto Daiichi Kagaku Co., Ltd., Kyoto, Japan

[21] Appl. No.: 598,528

[22] Filed: Feb. 8, 1996

[30] Foreign Application Priority Data

| Feb. 10, 1995 | [JP] | Japan | 7-059643 |
| Mar. 1, 1995 | [JP] | Japan | 7-080648 |
| Mar. 30, 1995 | [JP] | Japan | 7-109901 |

[51] Int. Cl.$^6$ ........................ B32B 31/16
[52] U.S. Cl. ............. 156/73.1; 156/290; 156/308.4; 156/309.6; 264/445
[58] Field of Search ............. 156/73.1, 290, 156/308.2, 308.4, 309.6, 580.1, 580.2; 264/442, 443, 445

[56] References Cited

U.S. PATENT DOCUMENTS

| 3,505,136 | 4/1970 | Attwood | 156/73.1 |
| 3,802,842 | 4/1974 | Lange et al. | 23/253 TP |
| 4,776,904 | 10/1988 | Charlton et al. | 156/73.1 |

FOREIGN PATENT DOCUMENTS

| 0209032 | 1/1987 | European Pat. Off. |
| 3442820 | 6/1985 | Germany |
| 53-6551 | 3/1978 | Japan |
| 01027928 | 1/1989 | Japan |
| 6-68488 | 8/1994 | Japan |

OTHER PUBLICATIONS

Branson Instruments, Inc., A Guide to Ultrasonic Plastics Assembly, pp. 10–11, Dec. 1974.

*Primary Examiner*—James Sells
*Attorney, Agent, or Firm*—Sughrue, Mion, Zinn, Macpeak & Seas, PLLC

[57] ABSTRACT

A method for fixing a reagent layer directly onto a supporting base plate in the preparation of a dry analysis kit for determining a specific component in a liquid specimen wherein at least one of the reagent layer and the base plate is a thermoplastic resin, and which comprises the steps of:

placing the reagent layer in contact with the base plate and externally applying ultrasonic vibration and pressure to the two layers to generate frictional heat thereby to melt the surface of the thermoplastic resin;

applying pressure to make the molten surface of thermoplastic resin bite the non-thermoplastic material or to integrate the surfaces of thermoplastic layer and base plate; and removing the ultrasonic vibration and pressure.

14 Claims, 4 Drawing Sheets

ULTRASONIC DIRECT FIXING OF REAGENT LAYER AND METHOD FOR PREPARING PEEL TYPE TEST PIECE

FIELD OF THE INVENTION

The present invention relates to a method for fixing a reagent layer to a supporting base in the preparation of a dry analysis kit for determining a specific component in a liquid specimen. Such a kit is usually used in the field of clinical examinations, such as an urine analysis, a serum analysis, a whole blood analysis, and an immunoassay.

The present invention relates also to a method for preparing a peel type test piece, which is a dry analysis kit for determining a specific component in whole blood, usually used in a whole blood analysis in the field of clinical examination.

BACKGROUND OF THE INVENTION

In the field of clinical examination, analyses of various components in body fluids, such as blood, urine, saliva, cerebrospinal fluid, etc., offer guides to diagnosis of many diseases or objective judgement of the efficacy of a treatment.

A general method of these analyses is one called wet chemistry, in which a body fluid (specimen) and a reagent solution are put in a cuvette and stirred, the cuvette is incubated at 37° C. for a given period of time, and a substance produced by the reaction of a specific component of the specimen is determined with an absorption photometer, a fluorophotometer, a turbidimeter, etc.

On the other hand, an analytical method called dry chemistry is being developed. This method is advantageous in that a reagent is supplied as a dry state, preparation of a reagent on analyses is not at all necessary, stirring is not necessary, no waste liquid occurs, and a very small amount of a specimen would be enough for analyses of many items. Dry chemistry has been made use of for instantaneous examinations in emergency laboratories of hospitals, nurses'offices in hospitals at night, or doctor's offices.

The dry analysis kit used in dry chemistry generally comprises a reagent layer and a supporting base plate. The reagent layer is prepared by infiltrating a reagent capable of reacting with a component in a specimen into a porous matrix such as paper, cloth, nonwoven cloth, meshes, membrane filters, sinters, and ceramics, followed by drying, or by applying a mixture of the reagent and a polymer binder kneaded with a solvent to a thin resin film, followed by drying. While the reagent layer cut into strips can be used as such, where an expensive reagent, such as an enzyme, a substrate, or a color former, is used, use of the strip as having a large effective area would be uneconomical, leading to a great increase in cost.

Accordingly, a reagent layer is cut into 4 to 10 mm squares or rectangles, taking into consideration the size allowing visual colorimetry, the diameter of a light beam used in reflective photometry, accuracy of measurement, and ease in handling in the preparation or on use. The cut reagent layer is fixed onto a base serving as base or grip with an adhesive, e.g., a double-sided adhesive tape, a paste adhesive or an instantaneous adhesive or a hot melt resin.

Moreover, of the dry analysis kits for dry chemistry, a so-called peel type test piece comprising a base having thereon a reagent layer and a releasable film layer having a sample measuring function in this order is used in some cases. Upon use, after a specimen is applied to the peel type test piece, the film layer is stripped off to observe the coloration of the reagent layer.

More specifically, a film layer capable of filtering out corpuscles of whole blood and measuring out an adequate amount of a specimen to the reagent layer is laminated on a reagent layer prepared by impregnating a matrix made of a thermoplastic resin or a non-thermoplastic substance with a reagent. When the dry analysis kit of this type is used, a specimen (whole blood) is applied on the film layer, the corpuscles and excess blood are wiped off the surface of the film layer, and the film layer is stripped to expose the reagent layer to observe the degree of coloration of the reagent layer. In some cases, the film layer is stripped without being wiped.

As stated above, the most commonly employed method for fixing a reagent layer directly to a base is fixation with a double-sided adhesive tape. However, double-sided adhesive tapes usually use polyacrylic resins, which contain no small amounts of polymerization initiators, monomers, stabilizers, plasticizers and wetting agents. On contact with the reagent layer, these components tend to react with the reagent in the reagent layer resulting in coloration or decomposition of the active ingredient. Therefore, strict selection of a double-sided adhesive tape has been required for each item.

Further, fixation with a double-sided adhesive tape has been accompanied with such disadvantages that the adhesive adheres to a processing machine to cause machine trouble and that the adhesive adheres to the surface of a reagent layer to make a part of the reagent layer unreactive with a specimen, resulting in unevenness of color formation.

In order to eliminate these problems associated with a double-sided adhesive tape, fixation with a hot-melt adhesive (an adhesive consisting of a thermoplastic resin which softens at 80° to 150° C. has been used. In this case, however, the whole reagent layer must be kept at 100° to 110° C. for several seconds to melt the hot-melt adhesive, which entertains a fear of denaturation of the reagent, particularly proteins, such as an enzyme, an antibody and an antigen. Additionally, the hot-melt adhesives contain plasticizers, stabilizers, and the like similarly to the double-sided adhesive tapes, and these components have adverse influences on the reagent.

A method comprising enveloping a reagent layer in fabric or a web and fusion bonding both sides of the envelope with a hot-melt adhesive has been suggested as a solution to the outstanding problems, as disclosed in JP-B-53-6551 (the term "JP-B" as used herein means an "examined published Japanese patent application"). The method consisting of enveloping a reagent layer in a nylon mesh and bonding both sides thereof with a hot-melt adhesive succeeds in solving the above-described two problems. However, there is a fear of the nylon mesh's getting loose due to shocks during transportation and, as a result, the reagent layer tends to move or come off. In addition, the method is troublesome and costly.

JP-B-6-68488 discloses a method for preparing a composition for detection, which comprises interposing a thermoplastic resin layer between a reagent layer and a base and cutting the laminate by means of a laser beam or ultrasonic waves to fix the cut area through fusion. This technique is for preparing a multi-layer kit for dry analysis without using an adhesive. However, the kit prepared is of the type that it is held by a clamping rod serving as a grip or placed on a holder on use. Further, margins cut off by a laser beam or ultrasonic waves go to waste. Moreover, a machine generating a laser beam or ultrasonic waves of sufficient power for cutting the laminate is required, and such a machine is generally expensive.

In particular, where a reagent layer to be fixed on a base is glass fiber filter paper, etc. having chemically bonded thereto an antibody, an antigen, an antibody-avidin-biotin complex, etc., which is used for microanalysis utilizing immune reaction (so-called dry immunoassay), use of a double-sided adhesive tape or a hot-melt adhesive gives rise to not only the above-mentioned problems but another problem that an unreacted component or a substance having an influence on the reaction is non-specifically adsorbed on the glass fiber filter paper to cause a great error.

Further, since the peel type test piece comprises at least three layers, the preparation process is troublesome because of involvement of two steps; one for adhering the first layer to the second layer, and then one for adhering the third layer to the second layer.

Furthermore, on removal of the film layer, it is necessary to be peeled between the film layer and the reagent layer. It is inconvenienced that the test pieces suffered peeling at the interface between the base and the reagent layer. Taking into consideration on this point, the adhesive strength between the reagent layer and the base should be stronger than the adhesive strength (hereinafter referred to as "interlaminar strength") between the reagent layer and the film layer. To make a difference in interlaminar strength between the two adhesive interfaces is troublesome.

The three layers laid one on the other can be adhered at a time while making a difference in interlaminar strength between the two adhesive interfaces by use of two kinds of adhesives. However, components used in adhesives tend to give adverse influences to the reagent in the reagent layer as mentioned above. Therefore, use of adhesives is not favorable.

Hence it has been demanded to develop an ideal method for preparing a peel type test piece, by which the three layers can be fixed at a time without using an adhesive while making a difference in interlaminar bond strength.

SUMMARY OF THE INVENTION

It has been found that the above problems in the preparation of a dry analysis kit are solved by using a thermoplastic resin as material of either one or both of a reagent layer and a supporting base plate and externally applying ultrasonic vibration and pressure to a combination of the reagent layer and the supporting base plate to generate frictional heat.

An ultrasonic fusion technique used in the present invention has the following advantages.

Differing from adhesion via an adhesive, a thermoplastic resin constituting a layer(s) is fused and fixed by frictional heat generated by ultrasonic waves. Therefore, the reagent in a reagent layer undergoes no influence of plasticizers or solvents present in adhesives. Since the heat is generated instantaneously on the surface of the layer and abated rapidly, the reagent in the reagent layer does not undergo denaturation.

The method is economical; for the reagent layer and the base are directly fixed together so that there is no margin to be cut off. Since the ultrasonic vibration used in the present invention is directly transmitted to the reagent layer, a relatively cheap ultrasonic oscillator will do.

Where a laminate composed of a plurality of thermoplastic resin layers or a combination of a thermoplastic resin layer and a non-thermoplastic porous layer is subjected to ultrasonication from one side thereof to cause ultrasonic fusion, the inventors of the present invention have found that, on comparing the interlaminar bond strength among interfaces, the interlaminar strength becomes higher as the interface gets closer to the side to which ultrasonic waves have been applied. The present invention has been completed by applying this principle to the preparation of a peel type test piece.

When three layers are fusion bonded at a time by means of an apparatus for generating heat and transmitting the heat directly to the layers, although the interface closer to the side to which heat is applied can be fixed, it is difficult to fix the interface farther from the side for the matter of heat conduction. Even if the farther interface may be fixed, the closer interface will have been destroyed by great heat by that time, and the reagent will have lost its activity completely.

According to the method of the present invention, to the contrary, heat is conducted to the layers not directly but indirectly. That is, ultrasonic vibration is transmitted to the layers to induce frictional heat. Thus, the above-described problems never arise.

The present invention thus provides quite a new method for preparing a dry analysis kit and a peel type test piece, which method is free from the disadvantages associated with conventional techniques while making effective use of all the advantages of ultrasonic fusion.

The object of the present invention is a method for fixing a reagent layer directly onto a supporting base plate in the preparation of a dry analysis kit for determining a specific component in a liquid specimen wherein at least one of the reagent layer and the base plate is a thermoplastic resin, and which comprises the steps of:

placing the reagent layer in contact with the base plate and externally applying ultrasonic vibration and pressure to the two layers to generate frictional heat thereby to melt the surface of the thermoplastic resin;

applying pressure to make the molten surface of thermoplastic resin bite the non-thermoplastic material or to integrate the surfaces of thermoplastic layer and base plate; and removing the ultrasonic vibration and pressure.

The fixation method according to the present invention can take various embodiments. Illustrative embodiments are shown below with reference numbers according to the accompanying drawings.

Embodiment 1

A method for fixing a reagent layer directly onto a supporting base plate in the preparation of a dry analysis kit for determining a specific component in a liquid specimen, which comprises the steps of:

placing the reagent layer (1) in contact with the base plate (2) and externally applying ultrasonic vibration and pressure to generate frictional heat thereby to melt either the surface of the base (2) in contact with the reagent layer (1) or the surface of the reagent layer (1) in contact with the base (2);

applying pressure to make the molten surface material of one of the layers bite the other layer; and removing the ultrasonic vibration and pressure.

In this embodiment, either one of supporting base (2) and reagent layer (1) is made of a thermoplastic resin, while the other is a porous matrix made of non-thermoplastic material. In other words, embodiment (1) includes two types; in one type base (2) is a thermoplastic resin plate while reagent layer (1) is a porous matrix made of non-thermoplastic material coated or impregnated with a reagent; and in the other type base (2) is a plate formed of a porous matrix made of non-thermoplastic material while reagent layer (1) is a thermoplastic resin film coated with a reagent.

In another embodiment, both a supporting base plate and a reagent layer may be made of thermoplastic resins as described below with reference numbers of the accompanying drawings.

Embodiment 2

A method for fixing a reagent layer directly onto a supporting base in the preparation of a dry analysis kit for determining a specific component in a liquid specimen, which comprises the steps of:

placing the reagent layer (4) in contact with the base (5) and externally applying ultrasonic vibration and pressure to generate frictional heat thereby to melt both the surface of the base (5) in contact with the reagent layer (4) and the surface of the reagent layer (4) in contact with the base (5);

applying pressure to integrate the molten surface of the base (5) and the molten surface of the reagent layer (4); and removing the ultrasonic vibration and pressure.

In this embodiment, both base (5) serving as a supporting base plate and reagent layer (4) are made of thermoplastic resins. Reagent layer (4) may take two forms; a porous matrix impregnated or coated with a reagent, and a thin resin film coated with a reagent. The integrated part of base (5) and reagent layer (4) is indicated by reference number (6) in FIG. 3.

One embodiment of the present invention is utilizing torsional ultrasonic waves.

Embodiment 3

A method for fixing a reagent layer comprising a very thin thermoplastic resin film coated with a reagent directly onto a supporting base in the preparation of a dry analysis kit for determining a specific component in a liquid specimen, which comprises the steps of:

placing the reagent layer in contact with the base and applying torsional ultrasonic vibration and external pressure to melt the surface of the reagent layer in contact with the base;

applying pressure to make the molten surface of the reagent layer bite the surface of the base or to integrate the molten surface of the reagent layer and the surface of the base;

removing the torsional ultrasonic vibration and pressure.

The terminology "torsional ultrasonic waves" as used herein denotes a concept characterized the most by having transverse vibration. The concept represented by this terminology makes contrast to that of the generally used terminology "ultrasonic waves" which means vertical vibration.

The conception of "torsional ultrasonic waves" would be understood easily by visualizing the scene of a glass's (having a circular mouth) being pressed to a plane with its mouth down while being rotated at a fixed position. The brim of the glass corresponds to a horn of an ultrasonic oscillator, and the torsional movement corresponds to transverse vibration.

Ordinary vertical ultrasonic vibration cannot melt a very thin thermoplastic resin film. On the other hand, torsional ultrasonic waves, which produce transverse vibration, can transmit vibration energy to the surface of a very thin film to melt the film due to its excellent energy efficiency. Since a transverse vibration has "scrub movement" also, it can completely fuse bond a very thin film to a base to provide a dry analysis kit having the film as a reagent layer. By the "scrub movement", the torsional ultrasonic wave can completely fuse bond a very thin film to a base even at small energy and low heat.

Embodiment 4

A method for preparing a peel type test piece for dry analysis for determining a specific component in a liquid specimen comprising a supporting base plate having thereon a reagent layer comprising a porous matrix impregnated with a reagent and further having thereon a releasable film layer having a function of filtering out corpuscles, the releasable film layer being to be stripped after application of a specimen to observe coloration of the reagent layer, which comprises the steps of:

superposing the reagent layer and the film layer on the supporting base plate in this order in mutual contact and applying ultrasonic vibration from the supporting base plate side;

applying pressure to make the surface of a molten layer bite the surface of an adjacent non molten layer or to integrate the surface material of a molten layer with the surface of an adjacent layer; and removing the ultrasonic vibration and pressure.

BRIEF DESCRIPTION OF DRAWINGS

In FIGS. 1 to 7, (1) . . . Reagent layer of Embodiment 1 (porous matrix coated or impregnated with a reagent) or Embodiment 3 (very thin layer coated with a reagent)

(2) . . . Base (thermoplastic resin plate or a porous matrix made of non-thermoplastic material)

(3) . . . Molten part of the base (resin)

(4) . . . Reagent layer of Embodiment 2 (thermoplastic resin film coated with a reagent)

(5) . . . Base (thermoplastic resin plate)

(6) . . . The molten parts of (4) and (5)

(7) . . . Fusion bonded part (streaks)

(8) . . . Fusion bonded part (spots avoiding the central portion of a reagent layer).

Figure 8A:
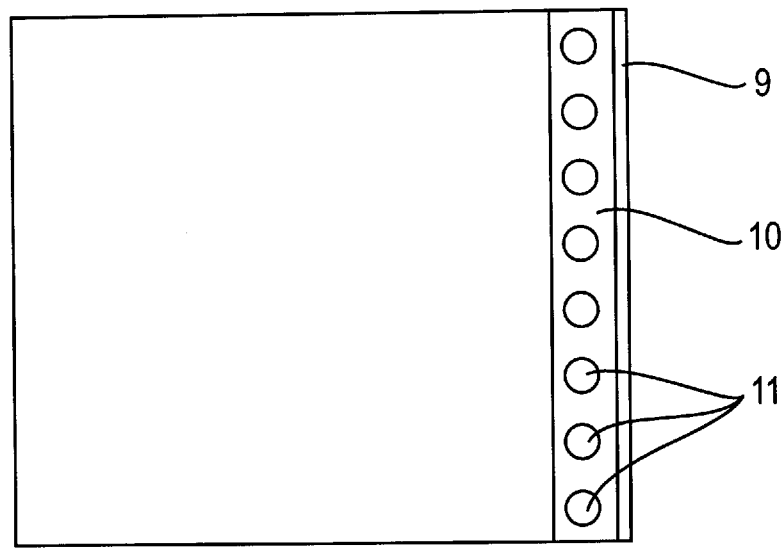
Figure 8B:

FIGS. 8A–8B provides a plane view (FIG. 8A) and a side view (FIG. 8B) of a dry analysis kit of Embodiment 3 according to the present invention in a state before cutting.

Figure 9:
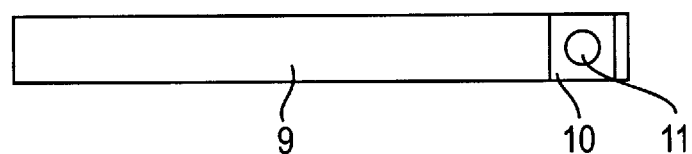

FIG. 9 is a plane view of a dry analysis kit according to Embodiment 3 according to the present invention in a state after cutting.

Figure 10:
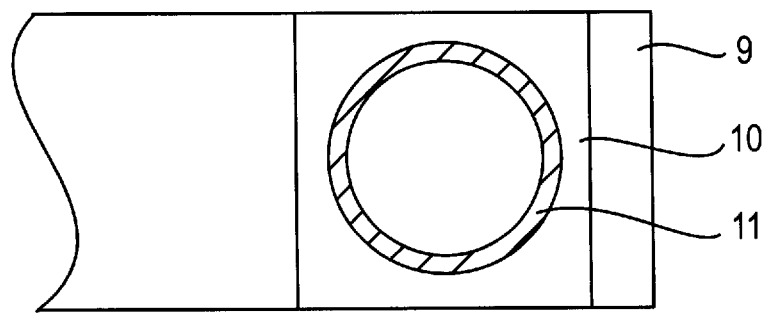

FIG. 10 is an enlarged plane view of the tip of the dry analysis kit shown in FIG. 9.

In FIGS. 8 to 10, (9) . . . Supporting base plate (base)
(10) . . . Reagent layer (very thin thermoplastic resin film)
(11) . . . Fusion bonded part.

Figure 11A:
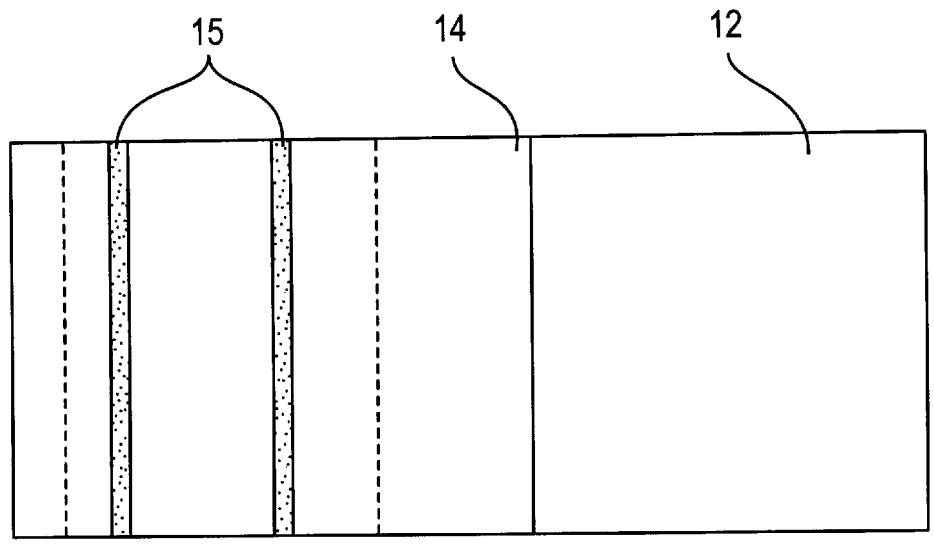
Figure 11B:
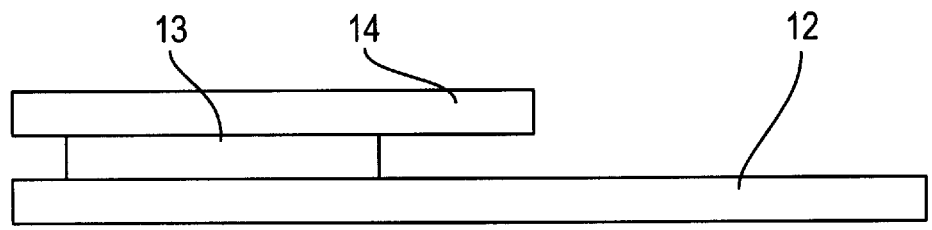

FIGS. 11A–11B show a plane view (FIG. 11A) and a cross sectional view (FIG. 11B) of a dry analysis kit of Embodiment 4 according to the present invention in a condition before cutting.

Figure 12:
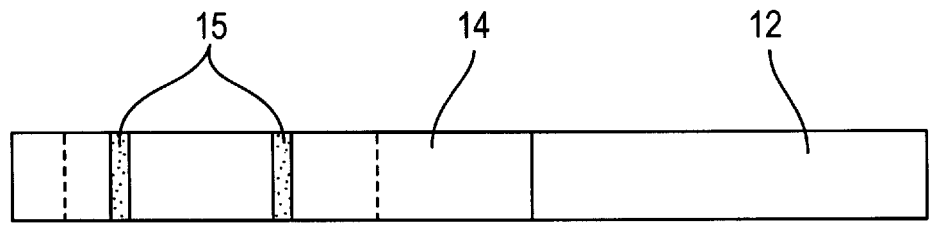

FIG. 12 is a plane view of the dry analysis kit of FIGS. 11A–B after cutting to 7 mm widths (the cross section is the same as FIG. 11B).

In FIGS. 11A–B and 12,

(12) . . . Supporting base plate (base)
(13) . . . Reagent layer (porous matrix)
(14) . . . Film layer
(15) . . . Ultrasonic fusion bonded part (streak).

To be easy to understand the structures of the present invention, the proportions of widths and thicknesses are appropriately modified in these figures.

DETAILED DESCRIPTION OF THE INVENTION

Whether made of a thermoplastic resin or a non-thermoplastic material, the base should have such a thickness that ensures sufficient strength for supporting a reagent layer to be fixed thereon. Such a thickness is decided in the same manner as with usual dry analysis kits. The base thickness is usually 0.1 to 0.4 mm.

The non-thermoplastic material include three-dimension lattice structural materials such as paper (filter), wood, nonwoven fabric such as a membrane filter, woven fabric, knit fabric, glass such as glass fiber filter, a sinter, ceramics such as porous ceramic sheet, metal cloth and polymer microbeads. It is preferable that these are porous matrix. It is essential that the material should not be fused by heat.

The thermoplastic resins which can be used in the supporting base plate or reagent layer can be selected from those generally employed in dry analysis kits of this kind. Preferable examples are polyethylene terephthalate (sometimes abbreviated as PET), polycarbonate, polypropylene, polyethylene, polystyrene, polyvinyl acetate, polyvinyl chloride and a cellulose ester. Examples of these forms are a uniaxially stretched porous film, a biaxially stretched porous film and an irradiated porous film.

Impregnation or coating of a porous matrix with a reagent and coating of a thermoplastic resin film with a reagent can be carried out in a conventionally employed method for the preparation of dry analysis kits. That is, a reagent of a given amount necessary for analysis is dissolved or dispersed in a solvent, and the solution or dispersion is infiltrated into a porous matrix by means of an impregnating apparatus, etc., or a reagent is kneaded with a solvent and a polymer binder, and the mixture is applied to a film by means of coating apparatus and dried in a drier.

A reagent layer and a supporting base plate are superposed, and ultrasonic vibration and a pressure are applied for several $10^{-1}$ seconds. The ultrasonic vibration having a frequency of 20 kHz and a pressure of 60 to 80 kg/cm$^2$ are preferable. The ultrasonic vibration was stopped, and the pressure application is continued for an additional period of several $10^{-1}$ seconds and then the pressure is removed. The reagent layer and the supporting base plate can thus be fixed together.

Figure 1:
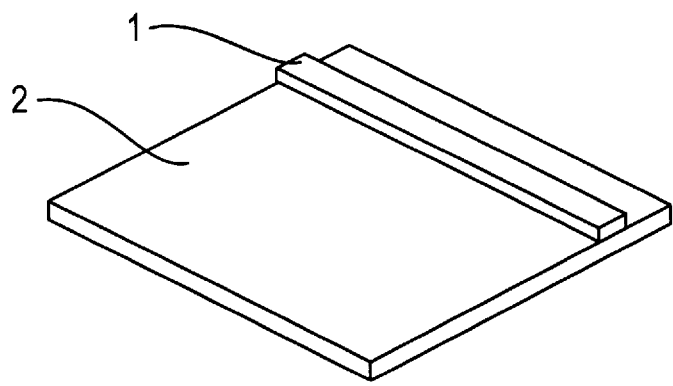
FIG. 1 is a perspective view of a dry analysis kit according to the present invention, which is common to Embodiments 1, 2 and 3, at the time when fixation of a reagent layer and a supporting base plate is completed.
Figure 2:
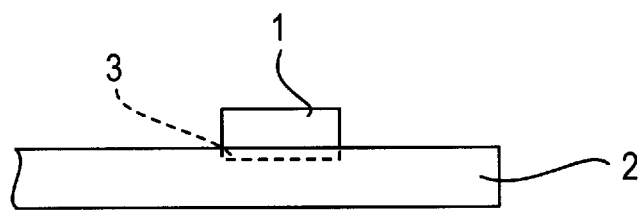
FIG. 2 is a cross section of a dry analysis kit according to Embodiment 1 of the present invention, showing the fixing condition.
Figure 3:
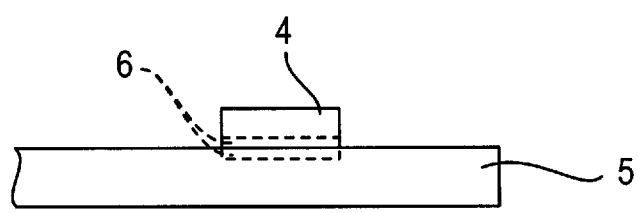
FIG. 3 is a cross section of a dry analysis kit according to Embodiment 2 of the present invention, showing the fixing condition.
Figure 4:
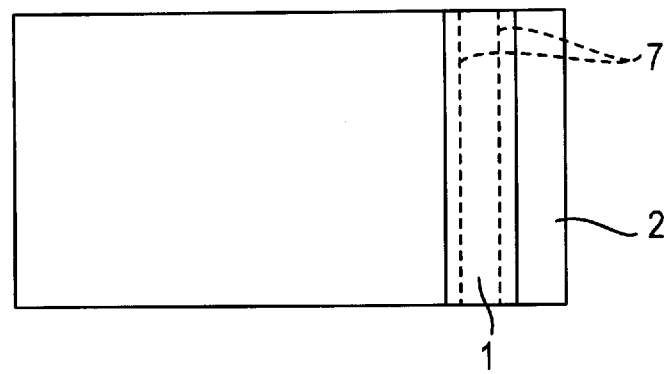
FIG. 4 is a plane view of the dry analysis kit of Example 1 of the present invention at the time when fixation is completed.
Figure 5:
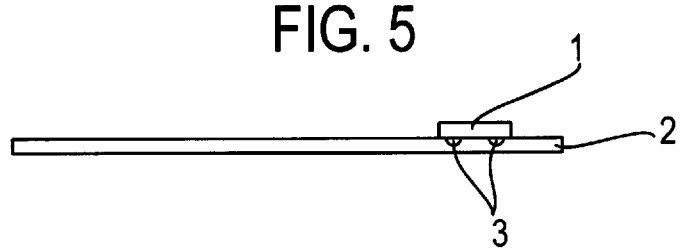
FIG. 5 is a cross section of the dry analysis kit of Example 1 of the present invention at the time when fixation is completed.
Figure 7:
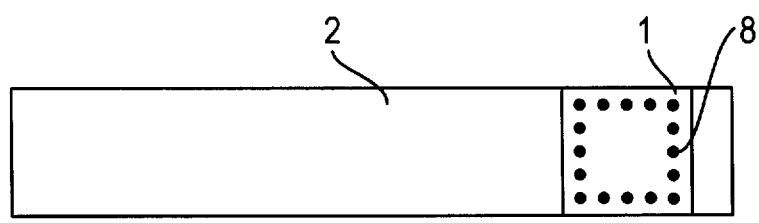
FIG. 7 is a plane view of a dry analysis kit in which a reagent layer is fixed by fusion at areas except the central portion.

In the case where all the contact area between a reagent layer and a supporting base plate is subjected to ultrasonic fusion, some influence of heat of fusion, though slight, may be exerted on the reagent. Although the influence is so slight as to need no countermeasure for avoidance, it is preferable that the reagent layer and the base are fusion bonded not over the entire surface of the reagent layer but at a plurality of spots. It can be avoided by, for example, applying ultrasonication only to the peripheral portion of the reagent layer in streaks or spots while avoiding the central portion. An example of such spot fusion is shown in FIG. 7. An example of such streaks fusion is shown in FIGS. 4 and 5.

The dry analysis kit according to Embodiment 1 can be prepared by, for example, impregnating filter paper with a reagent capable of color formation upon specific reaction with a substance under analysis in a liquid specimen, drying the impregnated filter paper to obtain a reagent layer, putting the reagent layer on a polyethylene terephthalate plate as a supporting base plate, and imposing pressure while applying ultrasonic waves, whereby the molten polyethylene terephthalate of the supporting base plate side bites the reagent layer to achieve complete fixation through what we call an anchoring effect.

In another type of the dry analysis kit of Embodiment 1, the reagent layer is prepared by, for example, coating a thin polyethylene terephthalate film with a kneaded mixture of a reagent capable of color formation upon specific reaction with a substance under analysis contained in a liquid specimen and a polymer binder, followed by drying. The reagent layer is put on a base made of a non-thermoplastic porous matrix, such as filter paper, and subjected to ultrasonication. It is the surface of the reagent layer thin film in contact with the base that is melted by ultrasonication. The molten polyethylene terephthalate bites the supporting base plate to achieve complete fixation through a so-called anchoring effect.

The thin polyethylene terephthalate film used for providing a reagent layer can have a thickness of 50 to 150 $\mu$m, which is usually used in the art.

When the dry analysis kit of the latter of Embodiment 1 is used in a dip system, an additional advantage will be offered. That is, when the dry analysis kit is dipped in a liquid specimen and taken out, excess of the liquid specimen is absorbed by the supporting base plate and prevented from migrating to the reagent layer.

The dry analysis kit according to Embodiment 2 can be prepared by, for example, coating a thin polyethylene terephthalate film with a kneaded mixture of a reagent capable of color formation upon specific reaction with a substance under analysis contained in a liquid specimen and a polymer binder, followed by drying to prepare a reagent layer, putting the reagent layer on a polyethylene terephthalate plate, and imposing pressure while applying ultrasonic waves. The molten polyethylene terephthalate of the reagent layer side and that of the base side are brought into contact and thus integrated. On temperature drop, the both are completely fixed together.

In Embodiment 3, in using a supporting base plate made of a thermoplastic resin, the molten resin of a reagent layer is integrated with a similarly ultrasonication-molten resin of the supporting base plate and thus fixed thereto. In using a supporting base plate made of a porous matrix made of non-thermoplastic material, the molten resin of a reagent layer bites into the pores of a supporting base plate to achieve fixation through a so-called anchoring effect.

A thin reagent layer and a supporting base plate are superposed, and torsional ultrasonic vibration and a pressure are applied for several $10^{-1}$ seconds. The torsional ultrasonic vibration having a frequency of 40 kHz and a pressure of 60 to 80 kg/cm$^2$ are preferable. The ultrasonic vibration was then stopped, and the pressure application is continued for an additional period of several 10$^{-1}$ seconds and then the pressure is removed. The reagent layer and the supporting base plate can thus be fixed together.

Further, in Embodiment 3, it is preferable that the thin thermoplastic resin film has a thickness of 10 to 50 μm.

Embodiment 4 of the present invention is a method for preparing a peel type test piece comprising a supporting base plate having thereon a reagent layer and further having thereon a releasable film layer having a sample measuring function. The material of each layer will be specified later.

In the Embodiment 4, where a thermoplastic resin layer and a porous matrix made of a non-thermoplastic material are adjacent to each other, it is an essential condition that the thermoplastic resin on the surface section of the former layer is melted by ultrasonic waves and the molten resin is made to bite the pores of the latter layer to achieve fixation by a so-called anchoring effect. Where two adjacent layers are both made of a thermoplastic resin and the surface resin of both the two layers is melted, it is an essential condition that the resins on the surface of the two layers are integrated into one body to achieve fixation.

Accordingly, of the three basic layers constituting a peel type test piece using a porous matrix as a reagent layer, it is essential that (1) all of them are made of thermoplastic resins, (2) two of them are made of thermoplastic resins, with the remaining one being a porous matrix made of non-thermoplastic material, or (3) the intermediate one of them is made of a thermoplastic resin, with the upper and lower layers being a porous matrix made of non-thermoplastic material. In other words, care should be taken so that a porous matrix made of non-thermoplastic material may not be adjacent to another porous matrix made of non-thermoplastic material.

In more detail, the peel type test piece of the present invention using a porous matrix as reagent layer embraces the following layer structures.

(1) All the supporting base plate, reagent layer and film layer are made of thermoplastic resins.

(2) The supporting base plate and film layer are made of thermoplastic resins, while the reagent layer is a porous matrix made of a non-thermoplastic material.

(3) The supporting base plate and film layer are a porous matrix made of non-thermoplastic material, while the reagent layer is a porous matrix made of a thermoplastic material.

(4) The supporting base plate and reagent layer are made of thermoplastic resins, while the film layer is a porous matrix made of a non-thermoplastic material.

The film layer is a matrix having a plurality of pores for securing an ability of filtering blood or an ability of retaining liquid. Alternatively, the film layer itself does not have pores but is equipped with a part having an ability of measuring out a specimen or retaining a specimen.

Examples of the method according to the present invention for preparing a dry analysis kit having a fixed reagent layer and peel type test piece will be illustrated by referring to the accompanying drawings. It should be understood that the present invention is not construed as being limited thereto.

EXAMPLE 1

A dry analysis kit for the detection of occult blood in urine was prepared as an example according to the following prescription.

| Prescription | |
|---|---|
| First impregnating solution: | |
| Potassium hydrogenphthalate buffer (0.5 M; pH 5.3) | 150 ml |
| Ethanol | 100 ml |
| Sodium lauryl sulfate | 200 mg |
| Ethylenediaminetetraacetic Acid Disodium Salt | 20 mg |
| Cumene hydroperoxide | 20 ml |
| Second impregnating solution: | |
| Ethanol | 80 ml |
| Xylene | 120 ml |
| 7-Methylquinoline | 1 ml |
| 3,3',5,5'-Tetramethylbenzidine | 1 g |

Porous matrix: 2Chr Filter Paper produced by Whatman
Base: 0.3 mm thick PET film The porous matrix was dipped in the first impregnating solution prepared according to the above formulation and dried, and subsequently dipped in the second impregnating solution and dried to obtain a reagent layer. The resulting reagent layer was placed on the base, and ultrasonic vibration at a frequency of 20 kHz and a pressure of 70 kg/cm$^2$ were applied thereto for 0.2 second. The ultrasonication was stopped, and pressure application was continued for an additional period of 0.2 second and removed.

Figure 6:
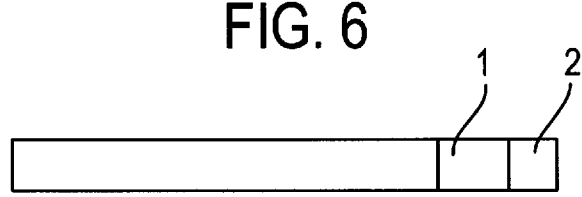
FIG. 6 is a plane view of a dry analysis kit of the present invention after completion of fixation and cutting into a strip.

In this example, the ultrasonic vibration was applied in streaks. The fusion condition is shown in FIGS. 4 and 5. The porous matrix having the reagent thus fixed thereto was slit to prescribed widths of 5 mm to obtain dry analysis kits as shown in FIG. 6.

COMPARATIVE EXAMPLE 1

For comparison, a reagent layer prepared according to the same formulation as in Example 1 was adhered to the base via a double-sided adhesive tape and cut to a prescribed size to obtain dry analysis kits.

Each of the dry analysis kits prepared above was put in a glass bottle and sealed together with a desiccant. The glass bottle was preserved at 50° C. for a prescribed period of time to conduct an accelerated test. As specimens, two beforehand prepared control urine preparations having different hemoglobin levels (0 mg/dl, designated preparation 1; and 0.2 mg/dl, designated preparation 2) were analyzed by means of an exclusive reflective photometer (spectral differential calorimeter SZ-Σ80, manufactured by Nippon Denshoku Kogyo K.K.). The results obtained are shown in Table 1 below.

TABLE 1

| | Reflectance (R %) | | | | | |
|---|---|---|---|---|---|---|
| | Hemoglobin Level | | | | | |
| | (Preparation 1) 0 mg/dl | | | (Preparation 2) 0.2 mg/dl | | |
| Days of Preservation | 0 (initial) | 7 | 14 | 0 (initial) | 7 | 14 |
| Ultrasonic Fusion | 97.4 | 96.0 | 94.5 | 19.0 | 20.8 | 22.2 |

TABLE 1-continued

| | Reflectance (R %) | | | | | |
|---|---|---|---|---|---|---|
| | Hemoglobin Level | | | | | |
| | (Preparation 1) 0 mg/dl | | | (Preparation 2) 0.2 mg/dl | | |
| Double-sided Adhesive Tape | 97.8 | 89.2 | 81.8 | 18.8 | 35.7 | 48.2 |

It is seen from Table 1 that the reflectance in the analysis of preparation 1 reduces with time. The reduction in reflectance means coloration of the reagent layer, indicating poor stability of the reagent layer. The increase in reflectance as observed with preparation 2 means reduction in sensitivity of the reagent layer, also indicating poor stability of the reagent layer. The results in Table 1 prove that the dry analysis kits prepared by the ultrasonic fusion fixation technique according to the present invention show a significant improvement in stability.

The reduction in stability is caused by the influences of components contained in the double-sided adhesive tape which make the analytical composition instable, such as an organic solvent and a plasticizer. To the contrary, the reagent layer fixed by ultrasonic fusion is not influenced by such components nor by the heat of fusion.

COMPARATIVE EXAMPLE 2

In order to examine the degree of influence by the heat of fixation, a reagent layer prepared and cut into strips in the same manner as in Example 1 but not fixed on a supporting base plate was prepared as a dry analysis kit and compared with the dry analysis kit of the present invention in the case where all the contact area between a reagent layer and a base plate. A beforehand prepared control urine preparation having a hemoglobin level of 0.2 mg/dl was analyzed as a specimen by means of an exclusive reflective photometer. Measurement was made 5 times for each dry analysis kit, and the results obtained are shown in Table 2 below.

TABLE 2

| | Reflectance (R %) | | | | | |
|---|---|---|---|---|---|---|
| | 1 | 2 | 3 | 4 | 5 | Average |
| Ultrasonic fused dry analysis kit | 19.5 | 20.2 | 18.5 | 17.3 | 19.5 | 19.0 |
| Dry analysis kit with no supporting base plate | 18.3 | 16.8 | 19.2 | 18.9 | 19.3 | 18.5 |

It is seen from Table 2 that the dry analysis kit prepared by ultrasonic fusion in the case where all the contact area between a reagent layer and a base plate gives substantially the equal results to those of the dry analysis kit with no supporting base plate, proving that the ultrasonic fusion according to the present invention gives very little of influence of heat to the reagent.

EXAMPLE 2

A dry analysis kit for the detection of nitrites in urine was prepared as an example according to the following prescription.

| Prescription | |
|---|---|
| d-Naphthylamine | 1.0 g |
| Sulfanilamide | 2.5 g |
| Trichloroacetic acid | 3.0 g |
| Polyvinyl butylacetal | 20.0 g |
| Methanol | 100 ml |
| Thermoplastic resin plate (used as supporting base plate (9)) . . . 0.3 mm thick PET film) | |
| Thermoplastic resin film (used as reagent layer (10)) . . . 1 cm wide and 20 μm thick PET film tape) | |
| Ultrasonic oscillator . . . 900 Series, Model 947M, manufactured by Emerson Japan Ltd. | |

A coating composition was prepared according to the above formulation and applied to the film with a coating machine to a thickness of 400 μm and dried in hot air to prepare a reagent layer (reagent layer (10)).

Reagent layer (10) was placed on base (9), and torsional ultrasonic vibration at a frequency of 40 kHz and a pressure of 70 kg/cm² were applied thereto for 0.2 second. The vibration was ceased, and pressure application was continued for an additional period of 0.2 second and then released.

The ultrasonic oscillation horn used had a cylindrical shape having an outer diameter of 6 mm and an inner diameter of 4 mm. As indicated by reference number (11) in FIGS. 8 to 10, the reagent layer was fixed by fusion in a circle in the peripheral portion thereof so as to avoid the central portion. The circle had an outer diameter of 6 mm and an inner diameter of 4 mm.

The thus prepared dry analysis kit shown FIG. 8 was cut into 1 cm wide strips to obtain dry analysis kits shown in FIG. 9.

On being dipped in nitrite-containing urine, the dry analysis kit satisfactorily assumed a red color in accordance with the nitrite content.

In the case of using a very thin film as in the above Example as a reagent layer, ordinary ultrasonication does not cause fusion whereas torsional ultrasonic waves can cause fusion as described above to prepare a dry analysis kit without involving activity reduction.

EXAMPLE 3

A peel type test piece was prepared as an example according to the following technique.
Base (supporting base plate)
    0.3 mm thick white polyethylene terephthalate film, produced by Teijin Ltd. (shown by reference number (12) in FIG. 11B)
Porous matrix (reagent layer)
    0.3 mm thick filter paper, 3MMChr produced by Whatman (shown by reference number (13) in FIG. 11B)
Film layer
    0.3 mm thick nylon mesh, produced by Teijin Ltd. (shown by reference number (14) in FIG. 11B)

A 7 mm wide reagent layer tape and a 10 mm wide film layer tape were placed on a 70 mm×360 mm base in the order described as shown in FIG. 11A. Ultrasonic vibration having a frequency of 20 kHz and a pressure of 70 kg/cm² were imposed to the base side for 0.2 second. After stopping application of ultrasonic vibration, pressure application was further continued for an additional period of 0.2 second and then released. The ultrasonic and pressure application was made in a streak form. The fixed part is shown by reference number (15) in FIG. 11A. Thereafter, the fixed layers were cut to 7 mm widths to obtain peel type test pieces shown in FIG. 12.

Test

Twenty test pieces were prepared. The film layer of each test piece was spotted with 10 μl of blue ink (aqueous ink for fountain pen) and wiped immediately after spotting. Sixty seconds later, the sample measuring layer (film layer) was peeled off.

Results

All the reagent layers of the twenty test pieces were found colored in blue. On removal of the film layer, none of the test pieces suffered peeling at the interface between the supporting base plate and the reagent layer instead of the interface between the film layer and the reagent layer.

Since the method of the present invention uses no adhesive (a double-sided adhesive tape, a hot-melt adhesive, etc.), no chemical influence is exerted on a reagent, and improvement in performance can be expected. Neither does the reagent undergo physical damage due to adhesion of a paste adhesive, etc. To use no adhesive results in cost reduction. From the standpoint of productive equipment, because a cheap ultrasonic oscillator may be used, the machinery can be made simpler and less expensive, and the steps involved are simplified, thus realizing reduction of production cost.

Further, even when such a very thin film that usual vibration energy cannot be concentrated is used as a reagent layer, the method of the present invention achieves ultrasonic fusion securely.

Moreover, as has been described in detail, the present invention makes it possible to fix three layers at a time without the aid of an adhesive while giving a difference between interfaces in interlaminar strength to prepare a peel type test piece. That is, the present invention provides quite a new method for preparing a peel type test piece, which method is free from the disadvantages associated with conventional techniques while making effective use of all the advantages of ultrasonic fusion.

While the invention has been described in detail and with reference to specific examples thereof, it will be apparent to one skilled in the art that various changes and modifications can be made therein without departing from the spirit and scope thereof.

What is claimed is:

1. A method for fixing a reagent layer directly onto a supporting base plate in the preparation of a dry analysis kit for determining a specific component in a liquid specimen wherein at least one of the reagent layer and the base plate is a thermoplastic resin, and which consists essentially of the steps of:

placing the reagent layer in contact with the base plate and externally applying ultrasonic vibrations and pressure to the two layers to generate frictional heat thereby to melt the surface of the thermoplastic resin;

applying pressure to make the molten surface of thermoplastic resin encroach and bond to the non-thermoplastic material or to integrate the surfaces of thermoplastic layer and base plate; and removing the ultrasonic vibrations and pressure.

2. A method according to claim 1, wherein said base plate is a thermoplastic resin, and said reagent layer is a porous matrix made of non-thermoplastic material.

3. A method according to claim 1, wherein said base plate is a porous matrix made of non-thermoplastic material, and said reagent layer is a film made of thermoplastic resin.

4. A method according to claim 1, wherein said base plate is a thermoplastic resin, and said reagent layer is a porous matrix or film made of thermoplastic resin.

5. A method according to claim 1, wherein said thermoplastic resin is selected from polyethylene terephthalate, polycarbonate, polypropylene, polyethylene, polystyrene, polyvinyl acetate, polyvinyl chloride or a cellulose ester.

6. A method according to claim 1, wherein said porous matrix made of non-thermoplastic material is selected from paper (filter), wood, nonwoven fabric such as a membrane filter, woven fabric, knit fabric, glass such as glass fiber filter, a sinter, ceramics such as porous ceramic sheet, metal cloth and polymer microbeads.

7. A method according to claim 1, wherein said reagent layer is a very thin thermoplastic resin film and said ultrasonic vibration is torsional ultrasonic vibration.

8. A method according to claim 7, wherein said thin thermoplastic resin film as the reagent layer has a thickness of 10 to 50 μm.

9. A method for preparing a peel type test piece for dry analysis for determining a specific component in a liquid specimen comprising a supporting base plate having thereon a reagent layer comprising a porous matrix impregnated with a reagent and further having thereon a releasable film layer having a function of filtering out corpuscles, the releasable film layer being to be stripped after application of a specimen to observe coloration of the reagent layer, which consists essentially of the steps of:

superposing the reagent layer and the film layer on the supporting base plate in this order in mutual contact and applying ultrasonic vibrations from the supporting base plate side;

applying pressure to make the surface of a molten layer encroach and bond to the surface of an adjacent non molten layer or to integrate the surface material of a molten layer with the surface of an adjacent layer; and removing the ultrasonic vibrations and pressure.

10. A method according to claim 9, wherein said base plate, said reagent layer, and said film layer are made of either a thermoplastic resin or a porous matrix made of non-thermoplastic material in such a manner that a layer made of a porous matrix made of non-thermoplastic material may not be adjacent to another layer made of a porous matrix made of non-thermoplastic material.

11. A method according to claim 9, wherein said film layer has a plurality of pores and has itself a measuring function or is equipped with a sample measuring part.

12. A method according to claim 10, wherein said thermoplastic resin is selected from polyethylene terephthalate, polycarbonate, polypropylene, polyethylene, polystyrene, polyvinyl acetate, polyvinyl chloride or a cellulose ester.

13. A method according to claim 10, wherein said porous matrix made of non-thermoplastic material is selected from paper (filter), wood, nonwoven fabric such as a membrane filter, woven fabric, knit fabric, glass such as glass fiber filter, a sinter, ceramics such as porous ceramic sheet, metal cloth and polymer microbeads.

14. A method for fixing a reagent layer directly onto a supporting base in the preparation of a dry analysis kit for determining a specific component in a liquid specimen, wherein at least one of the reagent layer and the base plate is a thermoplastic resin, which consists essentially of steps of:

(a) placing the reagent layer in contact with a plurality of discrete points on the base plate and externally applying ultrasonic vibrations and pressure to the two layers to generate functional heat thereby to melt the surface of the thermoplastic resin;

(b) applying pressure to make the molten surface of the thermoplastic resin encroach and bond to the non-thermal plastic material at the plurality of discrete points or to integrate a plurality of discrete points on the surfaces of thermoplastic layer and base plate; and (c) removing the ultrasonic vibrations and pressure.

* * * * *